(12) United States Patent
Sato

(10) Patent No.: US 11,478,305 B2
(45) Date of Patent: Oct. 25, 2022

(54) BEND INFORMATION COMPUTATION APPARATUS AND ENDOSCOPE SYSTEM

(71) Applicant: OLYMPUS CORPORATION, Tokyo (JP)

(72) Inventor: Ken Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1059 days.

(21) Appl. No.: 16/149,206

(22) Filed: Oct. 2, 2018

(65) Prior Publication Data

US 2019/0029763 A1    Jan. 31, 2019

Related U.S. Application Data

(63) Continuation of application No. PCT/JP2016/061166, filed on Apr. 5, 2016.

(51) Int. Cl.
*A61B 34/20* (2016.01)
*A61B 1/07* (2006.01)
(Continued)

(52) U.S. Cl.
CPC .......... *A61B 34/20* (2016.02); *A61B 1/00004* (2013.01); *A61B 1/005* (2013.01);
(Continued)

(58) Field of Classification Search
CPC ... A61B 34/20; A61B 1/00004; A61B 1/0017; A61B 1/005; A61B 1/07; A61B 2034/2061; G01B 11/16; G01B 11/24
See application file for complete search history.

(56) References Cited

U.S. PATENT DOCUMENTS 9,140,543 B1 * 9/2015 Allan ..................... G01B 11/16
9,239,429 B2 * 1/2016 Sakai ....................... A61B 1/07
(Continued)

FOREIGN PATENT DOCUMENTS

EP    0640819 A2 * 3/1995 ........... G01L 9/0077
EP    1564915 B1 * 11/2006 ........... H04B 10/572
(Continued)

OTHER PUBLICATIONS

English translation of International Preliminary Report on Patentability dated Oct. 18, 2018 together with the Written Opinion received in related International Application No. PCT/JP2016/061166.
(Continued)

*Primary Examiner* — Alexandra L Newton
*Assistant Examiner* — Shankar Raj Ghimire
(74) *Attorney, Agent, or Firm* — Scully, Scott, Murphy & Presser, P.C.

(57) ABSTRACT

A bend information computation apparatus includes a generation unit and a bend information arithmetic operator. The generation unit generates suppression information that suppresses first information representing a variation in spectrum not derived from a bend of a detection target provided in a light guide on the basis of light source spectrum information. The bend information arithmetic operator operates second information representing a variation in spectrum derived from the bend on the basis of a spectrum of light guided by the light guide, operates third information representing a variation in spectrum derived only from the bend on the basis of the second information and the suppression information, and operates bend information on the basis of the third information.

9 Claims, 7 Drawing Sheets

(51) Int. Cl.
*A61B 1/00* (2006.01)
*G01B 11/16* (2006.01)
*A61B 1/005* (2006.01)
*G01B 11/24* (2006.01)

(52) U.S. Cl.
CPC ............ *A61B 1/0017* (2013.01); *G01B 11/16* (2013.01); *G01B 11/24* (2013.01); *A61B 1/07* (2013.01); *A61B 2034/2061* (2016.02)

(56) References Cited

U.S. PATENT DOCUMENTS

| | | | | |
|---|---|---|---|---|
| 10,016,120 B2 * | 7/2018 | Fujita | | A61B 1/00 |
| 10,729,313 B2 * | 8/2020 | Sato | | A61B 5/065 |
| 10,809,750 B2 * | 10/2020 | Swanson | | A61B 5/0075 |
| 10,813,701 B2 * | 10/2020 | Sato | | A61B 1/0002 |
| 2007/0116415 A1 * | 5/2007 | Kobayashi | | A61B 5/065 |
| | | | | 385/116 |
| 2008/0212082 A1 * | 9/2008 | Froggatt | | G01D 5/353 |
| | | | | 356/73.1 |
| 2009/0122316 A1 | 5/2009 | Sperling et al. | | |
| 2009/0203966 A1 * | 8/2009 | Mizuyoshi | | G02B 23/26 |
| | | | | 600/182 |
| 2010/0191060 A1 * | 7/2010 | Shimotsu | | A61B 1/07 |
| | | | | 600/178 |
| 2011/0098533 A1 * | 4/2011 | Onoda | | A61B 5/065 |
| | | | | 600/117 |
| 2011/0144505 A1 * | 6/2011 | Yamamoto | | A61B 5/0064 |
| | | | | 600/476 |
| 2014/0036261 A1 * | 2/2014 | Fujita | | G02B 6/02052 |
| | | | | 356/300 |
| 2014/0111541 A1 * | 4/2014 | Tolkowsky | | A61M 25/09 |
| | | | | 345/632 |
| 2014/0166205 A1 * | 6/2014 | Tian | | H01J 37/32009 |
| | | | | 156/345.24 |
| 2016/0169663 A1 * | 6/2016 | Salomonsson | | G01B 11/16 |
| | | | | 700/259 |
| 2016/0287344 A1 * | 10/2016 | Donhowe | | A61B 1/009 |
| 2016/0331926 A1 * | 11/2016 | Bueche | | A61M 25/00 |
| 2017/0014055 A1 * | 1/2017 | Otani | | A61B 1/0653 |
| 2017/0020378 A1 * | 1/2017 | Godo | | H04N 5/2256 |

FOREIGN PATENT DOCUMENTS

| | | | | |
|---|---|---|---|---|
| JP | 2009-133848 A | 6/2009 | | |
| JP | 4714570 B2 | 6/2011 | | |
| JP | 2015-223440 A | 12/2015 | | |
| JP | 2016-007506 A | 1/2016 | | |
| WO | WO-2012137846 A1 * | 10/2012 | ............ | G01B 11/18 |
| WO | WO-2015198772 A1 * | 12/2015 | ............ | A61B 34/20 |

OTHER PUBLICATIONS

English translation of International Preliminary Report on Patentability dated Oct. 18, 2018 together with the Written Opinion received in related International Application No. PCT/JP2016/061040.

International Search Report dated Jun. 28, 2016 issued in PCT/JP2016/061166.

Japanese Office Action dated Jun. 18, 2019 in Japanese Patent Application No. 2018-510159.

* cited by examiner

BEND INFORMATION COMPUTATION APPARATUS AND ENDOSCOPE SYSTEM

CROSS-REFERENCE TO RELATED APPLICATIONS

This application is a Continuation Application of PCT Application No. PCT/JP2016/061166, filed Apr. 5, 2016, the entire contents of which are incorporated herein by reference.

BACKGROUND OF THE INVENTION

1. Field of the Invention

The present invention relates to a bend information computation apparatus that computes bend information representing a bend state of a flexible section having flexibility and an endoscope system having the bend information computation apparatus.

2. Description of the Related Art

There is known an apparatus, incorporated into a flexible insertion section of an insertion apparatus (for example, an endoscope), for detecting a bend state of the insertion section. For example, Japanese Patent No. 4714570 discloses an endoscope shape detection probe using an optical fiber. The probe includes the optical fiber that bends as one piece with an insertion portion of an endoscope. The optical fiber is provided with two optical modulators for detecting two-directional curvatures of, for example, an X direction and a Y direction, at a substantially identical position in the longitudinal direction of the optical fiber. The optical modulators modulate the intensity, etc. of wavelength components of light traveling through the optical fiber. The probe detects the curvature of the optical fiber at the optical modulators, accordingly the curvature of the insertion portion that bends as one piece with the optical fiber, based on the intensity, etc. of wavelength components before and after passage through the optical modulators.

BRIEF SUMMARY OF THE INVENTION

The present invention is directed to a bend information computation apparatus that arithmetically operates bend information representing a direction of bend and a magnitude of bend of at least one detection target provided in a light guide guiding light for detection. The bend information computation apparatus includes: a light source that emits the light to the light guide; a light detection sensor that detects a first spectrum that is a spectrum of the light guided by the light guide; a generation unit that includes a light source spectrum information storage that stores light source spectrum information, and generates suppression information that suppresses first variation information representing a variation in spectrum not derived from the bend of a detection target on the basis of the light source spectrum information; and a bend information arithmetic operator that arithmetically operates second variation information including the first variation information and representing a variation in spectrum derived from the bend on the basis of the first spectrum, arithmetically operates third variation information representing the second variation information not including the first variation information and representing a variation in spectrum derived only from the bend on the basis of the second variation information and the suppression information, and arithmetically operates the bend information on the basis of the third variation information.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, an embodiment of the present invention will be described in detail with reference to FIGS. 1A, 1B, and 2 to 10. In some of the figures, illustration of a part of a member is omitted for the sake of clarity of the figures.

Figure 1A:
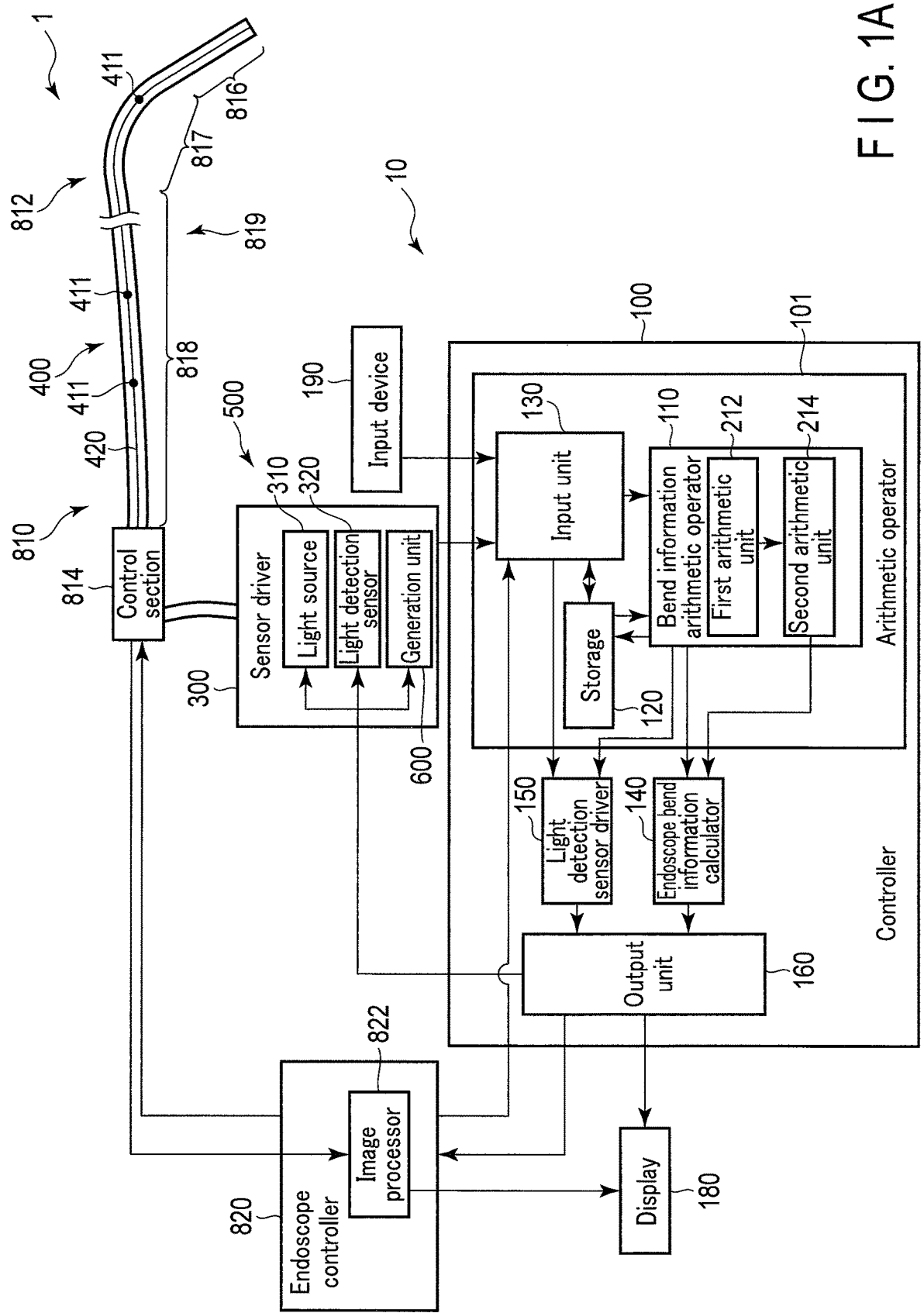
FIG. 1A is a diagram schematically showing a configuration of an endoscope system including a bend information computation apparatus according to an embodiment of the present invention.

As shown in FIG. 1A, an endoscope system 1 includes an endoscope 810, an endoscope controller 820, an input device 190, a display 180, and a bend information computation apparatus (hereinafter, referred to as a computation apparatus 10).

The endoscope 810 of the present embodiment is an example of an insertion apparatus to be inserted into an insertion target. The endoscope 810 will be described as a medical flexible endoscope, for example, but it is not necessary to be limited to this. The endoscope 810 only have to include a flexible insertion section 812 to be inserted into an internal portion of the insertion target, such as a flexible endoscope for industrial use, a catheter, and a treatment instrument, for example. The insertion target is not limited to a person, and may be an animal, or another structure, for example.

The endoscope 810 includes an insertion section 812 to be inserted into an insertion target, a control section 814 connected to a proximal end of the insertion section 812 to control the endoscope 810, and a cord (not shown) connected to the control section 814 and attachable to and detachable from the endoscope controller 820.

The insertion section 812 is, for example, hollow and elongated. The insertion section 812 includes, from a distal end to the proximal end of the insertion section 812, a distal hard section 816 in which various internal members according to the use of the endoscope 810 are disposed, a bendable section 817 capable of bending by a desired amount and in a desired direction, and a flexible tube section 818 having flexibility and capable of being bent by an external force. The internal members include, for example, an illumination optical system (not shown) and an image sensor (not shown).

The control section 814 is used for various operations of the endoscope 810 including the bendable section 817.

The endoscope controller 820 controls various operations of the endoscope 810, such as driving of the image sensor and dimming of illumination light. The endoscope controller 820 includes an image processor 822 that processes an image acquired by the image sensor.

The display 180 is a general display device, for example, a liquid crystal display, a CRT display, or an organic EL display. The display 180 is connected to the endoscope controller 820, and displays an image processed by the image processor 822. In addition, the display 180 is connected to a controller 100 (to be described later), and displays bend information, etc., obtained by the computation apparatus 10.

The input device 190 is a general device for input, for example, a keyboard, a pointing device such as a mouse, a tag reader, a button switch, a slider, and a dial. The input device 190 is connected to the controller 100. The input device 190 is used for a user to input various commands for operating the computation apparatus 10. The input device 190 may be a storage medium. In this case, information stored in the storage medium is input into the controller 100.

The computation apparatus 10 is a device for computing bend information representing a bend state of the insertion section 812, in particular, the bendable section 817 or the flexible tube section 818 (hereinafter, these are referred to as a flexible section 819).

Figure 1B:
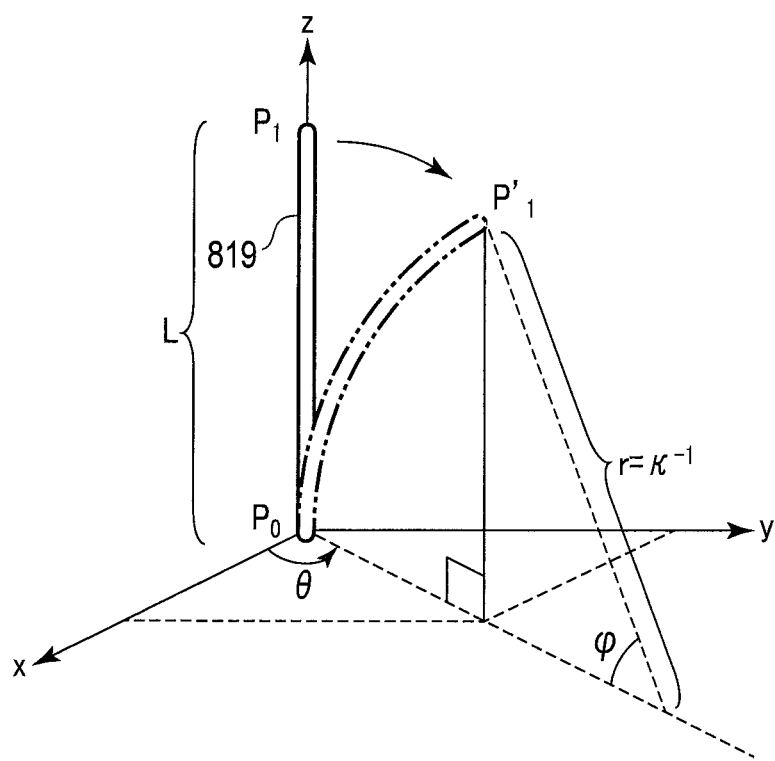
FIG. 1B is a diagram for explaining an amount representing a bend state of a flexible section.

The bend information will be explained with reference to FIG. 1B. FIG. 1B shows, by a solid line, the flexible section 819 with a length L, which is linearly positioned from an origin $P_0$ (0, 0, 0) to a point $P_1$ (0, 0, L). It is assumed that the flexible section 819 is bent as indicated by an imaginary line in FIG. 1B, and the point $P_1$ (0, 0, L) has displaced to a point $P'_1$ (x, y, z). Here, for the purpose of convenience, it is assumed that the flexible section 819 is bent in an arcuate shape. At this time, in order to express the bend state of the flexible section 819, two pieces of information, namely a direction of bend and a magnitude of bend, are necessary. The direction of bend is expressed by, for example, an angle θ formed between a straight line passing through a point (x, y, 0), at which the point $P'_1$ (x, y, z) is projected onto an xy plane, and the origin $P_0$ (0, 0, 0), and an x axis. In addition, the magnitude of bend is expressed by, for example, a curvature κ, a curvature radius $r=κ^{-1}$, or a central angle $φ=L/r=κL$. In this manner, in the present specification, the direction of bend and the magnitude of bend, which are necessary in order to express the bend state of the flexible section 819, are referred to as "bend information". For this purpose, the computation apparatus 10 computes bend information representing the direction of bend and the magnitude of bend of one or more detection targets 411 provided on a light guide 420 that guides light for detection, which will be described later.

As shown in FIG. 1A, the computation apparatus 10 includes a sensor 500 including a sensor driver 300 and a sensor assembly 400, and the controller 100. In the present embodiment, it is assumed that the sensor driver 300 is a separate body from the endoscope 810 and is connected to the endoscope 810. The sensor driver 300 may be incorporated into the control section 814. The sensor assembly 400 is incorporated into the endoscope 810 along its longitudinal direction.

Figure 2:
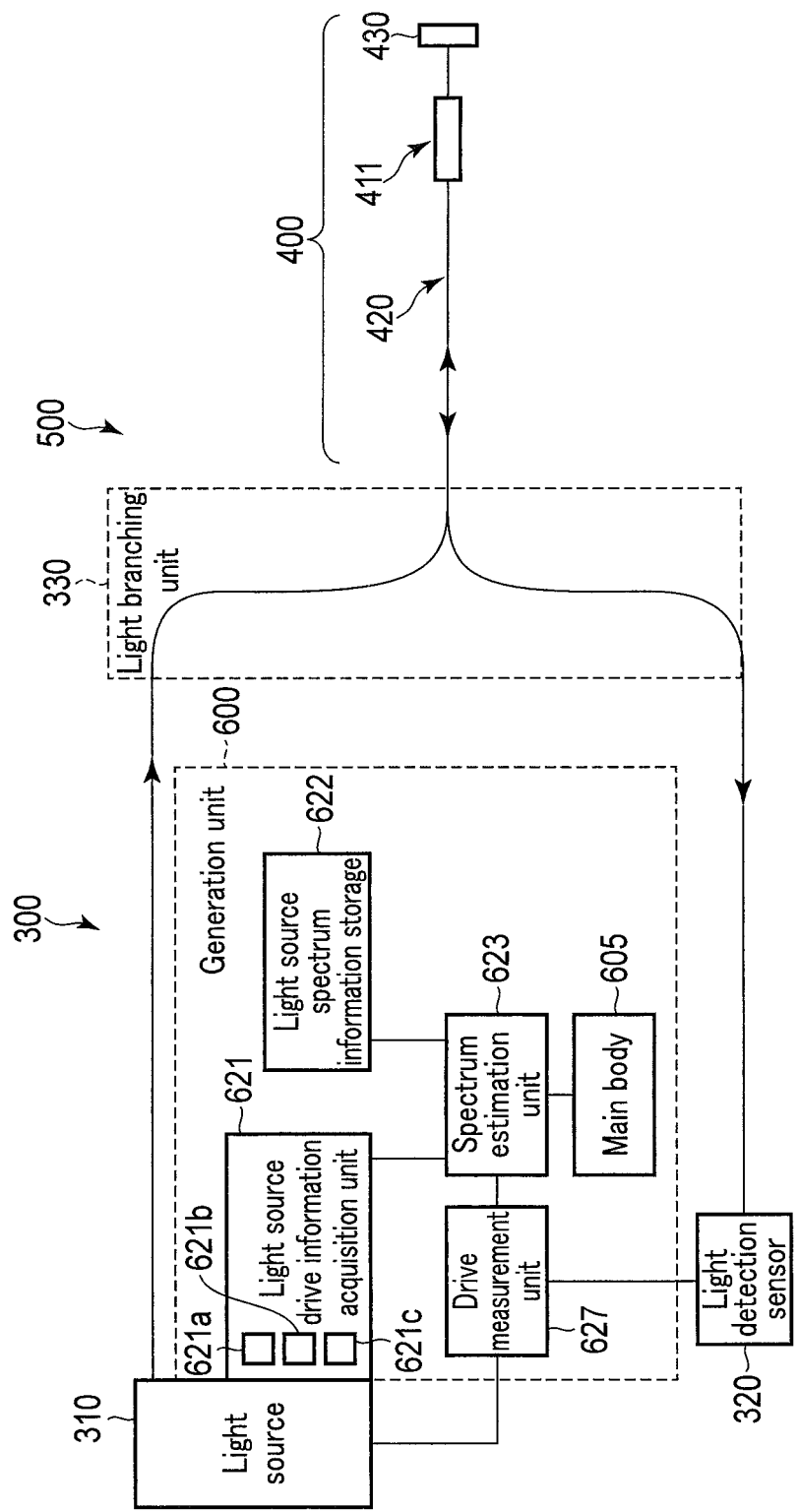
FIG. 2 is a block diagram showing an example of a sensor configuration.

As shown in FIGS. 1A and 2, the sensor driver 300 includes a light source 310, a light detection sensor 320, a light branching unit 330, and a generation unit 600. The sensor assembly 400 includes a light guide 420 provided with one or more detection targets 411, and a reflection member 430.

The light source 310 is, for example, a generally-known light emitting unit, such as a lamp, an LED, and a laser diode. The light source 310 may further include a phosphor, etc. for converting the wavelength. The light source 310 does not emit light for illumination supplied to the illumination optical system, but emits light for detection for the bend information to the light guide 420.

The light branching unit 330 is optically connected to the light source 310 and the light detection sensor 320. The light branching unit 330 includes, for example, an optical coupler or a beam splitter. The light branching unit 330 guides light emitted from the light source 310 to the light guide 420, and guides the light guided by the light guide 420 to the light detection sensor 320.

The light guide 420 is, for example, an optical fiber and has flexibility. A proximal end of the light guide 420 is connected to the light branching unit 330. The light guide 420 is incorporated into the insertion section 812 along its longitudinal direction, as schematically shown in FIG. 1A. In the light guide 420, the detection targets 411 are disposed at a portion of the insertion section 812 where it is desired to calculate the bend information, for example, at the flexible section 819. The detection targets 411 are disposed at positions that are mutually different in a longitudinal direction of the flexible section 819 or a circumferential direction of the flexible section 819.

Figure 3:
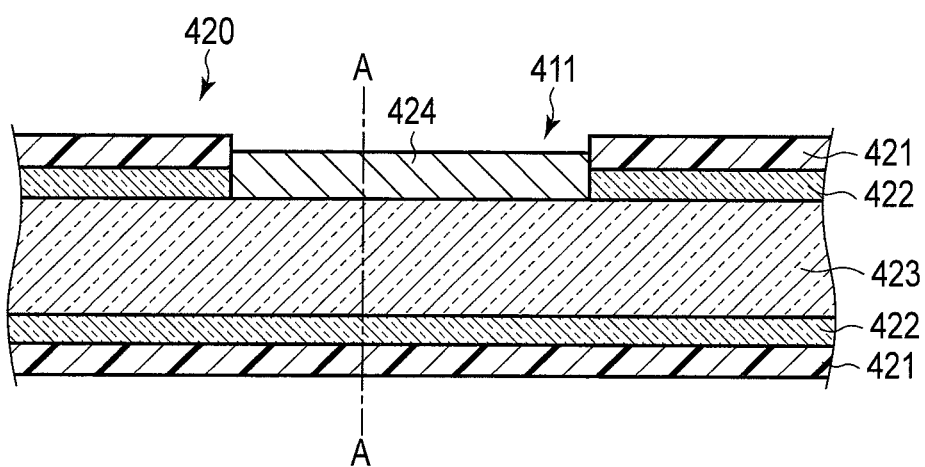
FIG. 3 is a longitudinal cross-sectional view of a light guide.
Figure 4:
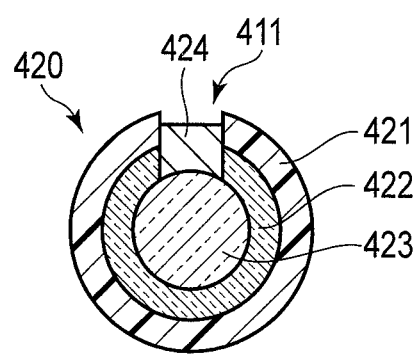
FIG. 4 is a transverse cross-sectional view of the light guide taken along a line A-A of FIG. 3.

FIG. 3 is a longitudinal cross-sectional view including an optical axis of the light guide 420. FIG. 4 is a cross-sectional view in a radial direction of the light guide 420 taken along the line A-A of FIG. 3. The light guide 420 includes a core 423, a cladding 422 surrounding the core 423, and a jacket 421 surrounding the cladding 422.

Each detection target 411 is formed by removing part of the jacket 421 and the cladding 422 to expose the core 423 and providing a light absorber 424 on the exposed core 423. The light absorber 424 absorbs part of the light guided by the light guide 420. An amount of light absorbed by the light absorber 424 varies depending on a bend state of the detection target 411. Characteristics of absorption spectra of the light absorbers 424 respectively provided in the detection targets 411 are different for each detection target 411.

A relationship between the bend state of the detection target 411 and a transmission quantity of light guided by the light guide 420 will be briefly described. When the light guide 420 is in a linear state, part of the light guided by the light guide 420 is absorbed by the light absorber 424. In contrast, when the light guide 420 bends so that the light absorber 424 faces inward, a quantity of light striking the light absorber 424 decreases, so that the quantity of light absorbed by the light absorber 424 decreases. Thus, as compared with the case where the light guide 420 is in the linear state, the transmission quantity of the light guided by the light guide 420 increases. On the other hand, when the light guide 420 bends so that the detection target 411 faces outward, the quantity of light striking the light absorber 424 increases, so that the quantity of light absorbed by the light absorber 424 increases. Thus, as compared with the case where the light guide 420 is in the linear state, the transmission quantity of light guided by the light guide 420 decreases. A degree of the transmission quantity corresponds to a bend amount of the light guide 420.

In this way, the quantity of light guided by the light guide 420 varies according to the bend state of the detection target 411. In other words, the detection target 411 functions as an optical modulator that modulates the light guided by the light guide 420 according to the bend state of the flexible section 819.

It is not limited to the light absorber 424, and an optical member that gives influence on the spectrum of the guided light can be used, and the optical member may be, for example, a wavelength converting member. In other words, the detection target 411 may be composed of a substance that absorbs light guided by the light guide 420 to emit light of a wavelength range that is different from the wavelength range of the guided light, such as a fluorescent material.

As shown in FIG. 2, the reflection member 430 is provided at an end of the light guide 420, that is, a tip end thereof, on the side on which the light guide 420 is not connected to the light branching unit 330. The reflection member 430 reflects the light guided from the light branching unit 330 by the light guide 420 so that the light travels back toward the light branching unit 330.

The light detection sensor 320 is a detector that detects light intensity for each wavelength. The light detection sensor 320 is, for example, a spectroscope. The light detection sensor 320 detects a first spectrum that is a spectrum of the light guided by the light guide 420 after being reflected by the reflection member 430. The first spectrum is output to the controller 100, and is stored in a storage 120 through an input unit 130 in the controller 100. Here, the first spectrum is detected light quantity information representing light intensity for each wavelength in a predetermined wavelength range.

The light detection sensor is not limited to a light detection sensor having spectroscopic characteristics. The light source and the light detection sensor include an aspect in which a quantity of light in each of predetermined wavelength ranges is detected by a combination of a light source and a light detection sensor. For example, the light source and the light detection sensor include an aspect in which narrowband light is emitted sequentially in time from a light source and a quantity of light in each wavelength range is detected by a broadband light detection sensor.

The light branching unit 330 and the reflection member 430 may be omitted. In this case, the light guide 420 is arranged in, for example, a U shape, the light source 310 is disposed at one end of the light guide 420, the light detection sensor 320 is disposed at the other end of the light guide 420, and the light guide 420 may be, for example, folded back at a desired position of the insertion section 812.

The generation unit 600 generates suppression information that suppresses first variation information in second variation information. Generation of the suppression information will be described later.

The first variation information represents, for example, a variation in spectrum not derived from bends of the detection targets 411. An example of the variation in spectrum not derived from the bends of the detection targets 411 is, for example, a variation in spectrum of the light source 310. The spectrum of the light source 310 (hereinafter, referred to as a second spectrum) is, for example, a spectrum of light immediately after being emitted from the light source 310, the light not being modulated by the detection targets 411. The second spectrum is detected light quantity information representing light intensity for each wavelength in a predetermined wavelength range.

The second variation information includes the first variation information, and represents a variation in spectrum derived from the bends of the detection targets 411. The second variation information is generated by a bend information arithmetic operator 110 (to be described later) on the basis of the first spectrum stored in the storage 120.

In the present embodiment, as will be described later, a variation in spectrum derived only from the bends of the detection targets 411 is represented as third variation information. That is, the third variation information is information obtained by removing the first variation information from the second variation information, and represents the second variation information not including the first variation information. In other words, in the second variation information, the first variation information not derived from the bend is overlapped on the third variation information derived only from the bend.

The generation unit 600 causes the second spectrum to be known. As shown in FIG. 2, the generation unit 600 includes a light source drive information acquisition unit 621, a light source spectrum information storage 622, a spectrum estimation unit 623, and a generation main body (hereinafter, referred to as a main body 605).

The light source drive information acquisition unit 621 acquires light source drive information of the light source 310. It is most preferable that the light source drive information includes all of drive current information of the light source 310 including a drive current of the light source 310, temperature information of the light source 310 including a temperature of the light source 310, and integrated drive time information of the light source 310 including an integrated drive time of the light source 310. The light source drive information acquisition unit 621 acquires a current status of the light source 310, such as a drive current, a temperature, and an integrated drive time. The light source drive information acquisition unit 621 outputs the acquired light source drive information to the spectrum estimation unit 623. The light source drive information may include at least one of the drive current information, temperature information, and integrated drive time information. It is preferable that the light source drive information includes at least the temperature information.

The light source drive information acquisition unit 621 includes a current detection unit 621a that detects the drive current of the light source 310. For example, the current detection unit 621a may detect a drive current flowing from the controller 100 to the light source 310. The current detection unit 621a includes, for example, a current detection sensor. For example, the current detection unit 621a may detect an instruction value of the drive current input from the input device 190 to the controller 100.

The light source drive information acquisition unit 621 includes a temperature measurement unit 621b that measures a temperature of the light source 310. The temperature measurement unit 621b is, for example, disposed near the light source 310. The temperature measurement unit 621b may measure an ambient temperature around the light source 310. The temperature measurement unit 621b may be disposed at a heat generating portion that generates the most heat in the light source 310, and may measure the temperature of the heat generating portion. For example, the heat generating portion may be disposed in an emission portion of the light source 310 that emits a primary light toward the light branching unit 330, or in a light emitting element provided in the light source 310. The temperature measurement unit 621b includes, for example, a temperature sensor.

The light source drive information acquisition unit 621 includes a time measurement unit 621c that measures the integrated drive time of the light source 310. For example, the time measurement unit 621c measures the integrated drive time that the light detection sensor 320 is cumulatively driving, and regards the measured integrated drive time of the light detection sensor 320 as the integrated drive time of the light source 310. The time measurement unit 621c includes, for example, a timer.

The light source drive information acquisition unit 621 includes the current detection unit 621a, the temperature measurement unit 621b, and the time measurement unit 621c, according to information to be acquired.

A light source spectrum information storage 622 stores light source spectrum information. The light source spectrum information includes a relationship between the light source drive information and the second spectrum (the spectrum of the light source 310). This relationship shows, for example, the second spectrum corresponding to each of the drive current, the temperature, and the integrated drive time of the light source 310.

When the light source drive information is input from the light source drive information acquisition unit 621, the spectrum estimation unit 623 accesses the light source spectrum information storage 622. Then, the spectrum estimation unit 623 estimates the second spectrum by reading the second spectrum corresponding to the light source drive information from the light source spectrum information storage 622. As described above, the spectrum estimation unit 623 estimates the second spectrum as a spectrum of light emitted by the light source 310, on the basis of the light source drive information acquired by the light source drive information acquisition unit 621 and the light source spectrum information stored in the light source spectrum information storage 622. The spectrum estimation unit 623 outputs the estimated second spectrum to the main body 605. The spectrum estimation unit 623 is configured by, for example, a hardware circuit including an ASIC, etc. The spectrum estimation unit 623 may be configured by a processor. In the case where the spectrum estimation unit 623 is configured by a processor, a program code for causing the processor to function as the spectrum estimation unit 623 by being executed by the processor, has been stored in an internal memory or an external memory (not shown) accessible by the processor.

The main body 605 generates the first variation information on the basis of the second spectrum. It is also feasible that the spectrum estimation unit 623 outputs the second spectrum to the controller 100, and the bend information arithmetic operator 110 generates the first variation information in the controller 100. Alternatively, the second spectrum may be stored in the storage 120. In this case, the main body 605 or the bend information arithmetic operator 110 may generate the first variation information on the basis of the second spectrum stored in the storage 120. In the case where the first variation information is generated by the bend information arithmetic operator 110, the first variation information may be output to the main body 605 through an output unit 160 to be described later, or may be stored in the storage 120 and then read to the main body 605.

The generation unit 600 further includes a drive measurement unit 627 that measures at least one of the integrated drive time and the number of times of integrated drive of at least one of the light source 310 and the light detection sensor 320, and outputs a measurement result to the spectrum estimation unit 623. It is preferable that the drive measurement unit 627 measures at least one of the integrated drive time and the number of times of integrated drive of the light source 310. The drive measurement unit 627 may be disposed outside the generation unit 600 and inside the sensor driver 300. The drive measurement unit 627 includes, for example, a counter. The spectrum estimation unit 623 is controlled to turn its driving on or off on the basis of a measurement result of the drive measurement unit 627 and a threshold value stored in a storage (not shown). The threshold value is, for example, a reference value for the integrated drive time of the light source 310.

The main body 605 generates suppression information on the basis of the first variation information, and outputs it to the controller 100. Generation of the suppression information will be described later. The main body 605 is, for example, configured by a hardware circuit including an ASIC, etc. The main body 605 may be configured by a processor. In the case where the main body 605 is configured by a processor, a program code for causing the processor to function as the main body 605 by being executed by the processor, has been stored in the internal memory or the external memory (not shown) accessible by the processor. The main body 605 may be disposed in the controller 100. The main body 605 may be included in the bend information arithmetic operator 110.

Next, the controller 100 of the computation apparatus 10 will be described again referring to FIG. 1A. The controller 100 includes an arithmetic operator 101, an endoscope bend information calculator 140, a light detection sensor driver 150, and the output unit 160.

The arithmetic operator 101 is configured by, for example, a hardware circuit including an ASIC, etc. The arithmetic operator 101 may be configured by a processor. In the case where the arithmetic operator 101 is configured by a processor, a program code for causing the processor to function as the arithmetic operator 101 by being executed by the processor, has been stored in the internal memory or the external memory (not shown) accessible by the processor. The arithmetic operator 101 includes the input unit 130, the storage 120, and the bend information arithmetic operator 110.

For example, the first spectrum from the light detection sensor 320 and the suppression information from the main body 605 are input into the input unit 130. The input unit 130 transmits the input first spectrum and suppression information to the bend information arithmetic operator 110. In addition, into the input unit 130, a light quantity information relationship (to be described later) of each of the detection targets 411 may be input from the input device 190. Furthermore, the information output from the endoscope controller 820 is also input into the input unit 130. The input unit 130 transmits the input information to the bend information arithmetic operator 110 or the light detection sensor driver 150.

The storage 120 further stores various kinds of information necessary for arithmetic operations performed by the bend information arithmetic operator 110. The storage 120 stores, for example, a program including a calculation algorithm and light quantity information relationship of the detection target 411.

The light quantity information relationship shows the absorption spectrum of the light absorber 424 disposed in each of the detection targets 411 and a relationship between the intensity of light modulated by each of the detection targets 411 and the bend information.

The bend information arithmetic operator 110 generates the second variation information. The bend information arithmetic operator 110 calculates the bend information of each detection target 411 based on the second variation information, the suppression information generated by the main body 605, and the light quantity information relationship stored in the storage 120. The bend information arithmetic operator 110 includes a first arithmetic unit 212 and a second arithmetic unit 214. The first arithmetic unit 212 calculates the third variation information (bend variation ratio) for each detection target 411 based on the second variation information and the suppression information, and the light quantity information relationship stored in the storage 120. Based on the third variation information (bend variation ratio) calculated by the first arithmetic unit 212 and the bend information stored in the storage 120, the second arithmetic unit 214 calculates the bend information at each detection target 411. The bend information stored in the storage 120 indicates information showing a relationship between the third variation information (bend variation ratio) and the bend information in each detection target 411. The bend information arithmetic operator 110 transmits the calculated bend information to the endoscope bend information calculator 140. In addition, the bend information arithmetic operator 110 outputs information on the operation of the light detection sensor 320 to the light detection sensor driver 150.

The endoscope bend information calculator 140 is, for example, configured by a hardware circuit including an ASIC, etc. The endoscope bend information calculator 140 may be configured by a processor. In the case where the endoscope bend information calculator 140 is configured by a processor, a program code for causing the processor to function as the endoscope bend information calculator 140 by being executed by the processor, has been stored in the internal memory or the external memory (not shown) accessible by the processor. Based on the bend information of the detection target 411 arithmetically operated by the bend information arithmetic operator 110, the endoscope bend information calculator 140 calculates the bend information of the insertion section 812 where the detection targets 411 are disposed. The calculated bend information of the insertion section 812 is transmitted to the output unit 160. The endoscope bend information calculator 140 may be incorporated into the bend information arithmetic operator 110.

The bend information of each detection target 411 is transmitted from the endoscope bend information calculator 140 to the output unit 160. The bend information of each detection target 411 may be transmitted from the bend information arithmetic operator 110 to the output unit 160.

Based on the information acquired from the input unit 130 and the bend information arithmetic operator 110, the light detection sensor driver 150 generates driving signals for the light detection sensor 320 and the spectrum estimation unit 623. By the driving signals, the light detection sensor driver 150 can, for example, switch on/off the operation of the light detection sensor 320 and the spectrum estimation unit 623 based on the user's instruction acquired through the input unit 130, and can adjust a gain of the light detection sensor 320 based on the information acquired from the bend information arithmetic operator 110. In addition, the light detection sensor driver 150 may be configured to be able to generate a driving signal that also controls the operation of the light source 310. The light detection sensor driver 150 transmits the generated driving signal to the output unit 160.

The output unit 160 outputs the bend information of the detection target 411 acquired from the endoscope bend information calculator 140 and the bend information of the insertion section 812 acquired from the endoscope bend information calculator 140 to the display 180. In addition, the output unit 160 outputs the acquired bend information to the endoscope controller 820. The output unit 160 also outputs the driving signals from the light detection sensor driver 150 to the light source 310, the light detection sensor 320, and the spectrum estimation unit 623.

The operations of the endoscope system 1 and the computation apparatus 10 of the present embodiment will be described.

The insertion section 812 of the endoscope 810 is inserted into the insertion target by the user. At this time, the insertion section 812 bends following the shape of the insertion target. The endoscope 810 acquires an image signal by an observation optical system and the image sensor in the insertion section 812. The acquired image signal is transmitted to the image processor 822 of the endoscope controller 820. The image processor 822 creates an image inside the insertion target based on the acquired image signal. The image processor 822 displays the created image on the display 180.

When the user wishes to display the bend information of the insertion section 812 on the display 180, or when the user wishes to cause the endoscope controller 820 to perform various operations using the bend information of the insertion section 812, the user inputs instructions to the controller 100 by the input device 190. At this time, the computation apparatus 10 operates.

When the computation apparatus 10 operates, the light source 310 of the sensor driver 300 emits light in a predetermined emission wavelength range. The light emitted from the light source 310 is guided to the light guide 420 of the sensor assembly 400 through the light branching unit 330. The guided light is guided by the light guide 420 from the base end side to the tip end side. At this time, the light quantity in the light guide 420 varies in accordance with bend states of the detection targets 411 provided on the light guide 420, and the quantity of guided light varies at each wavelength. Then, the light is reflected and returned by the reflection member 430, and is guided by the light guide 420 from the tip end side to the base end side. At this time, in the reflected light, the light quantity again varies depending on the detection target 411, and the quantity of transmitted light varies at each wavelength. That is, the reflected light is again subjected to the light quantity variation by the detection targets 411. The reflected light reaches the light detection sensor 320 through the light branching unit 330. The light detection sensor 320 detects intensity of the reached light at each wavelength.

The light detection sensor 320 detects the first spectrum representing the intensity of light at each wavelength. The bend information arithmetic operator 110 generates the second variation information on the basis of the first spectrum.

When the light source 310 is driven, the light source drive information acquisition unit 621 acquires the light source drive information, and outputs the acquired light source drive information to the spectrum estimation unit 623. When the light source drive information is input into the spectrum estimation unit 623 from the light source drive information acquisition unit 621, the spectrum estimation unit 623 accesses the light source spectrum information storage 622. Then, the spectrum estimation unit 623 estimates the second spectrum by reading the second spectrum (the spectrum of the light source 310) corresponding to the light source drive information from the light source spectrum information storage 622. In this way, the second spectrum that is a spectrum of light emitted from the light source 310 is estimated by the spectrum estimation unit 623 on the basis of the light source drive information acquired by the light source drive information acquisition unit 621 and the light source spectrum information stored in the light source spectrum information storage 622.

Here, operations of the light detection sensor 320, the generation unit 600, and the bend information arithmetic operator 110 will be described.

Hereinafter, at the time T0, the detection targets 411 are each in the reference state, for example, a linear state.

First of all, first spectra I0 and I1 at times T0 and T1 will be described.

The time T1 is a time when a predetermined time has elapsed from the time T0. At the time T1, the detection targets 411 are in a varied state varied with respect to the reference state, for example, a bend state.

Figure 5:
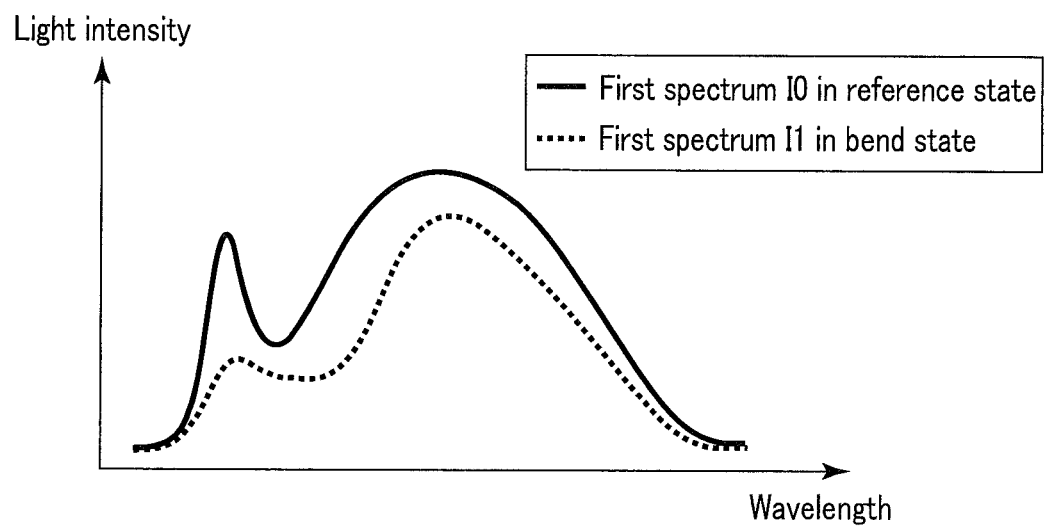
FIG. 5 is a diagram showing, in terms of a first spectrum representing a light intensity for each wavelength in a predetermined wavelength range, a relationship between a first spectrum I0 in a reference state and a first spectrum I1 in a bend state.

FIG. 5 shows a relationship between the first spectra I0 and I1, which are light intensities for respective wavelengths in a predetermined wavelength range detected by the first light detection sensor 320 at the time T0 and time T1. The first spectrum I0 at the time T0 indicates a spectrum when the detection targets 411 are in the reference state. The first spectrum I1 at the time T1 indicates a spectrum when the detection targets 411 are in the bend state. When a detection target 411 bends, the light quantity absorbed by the light absorber 424 varies depending on the direction of bend and the magnitude of bend. Here, it is assumed that the variation (the first variation information) of the spectrum of the light source 310 is not considered.

Next, variation ratios of the first spectra I0 and I1 will be described.

Figure 6:
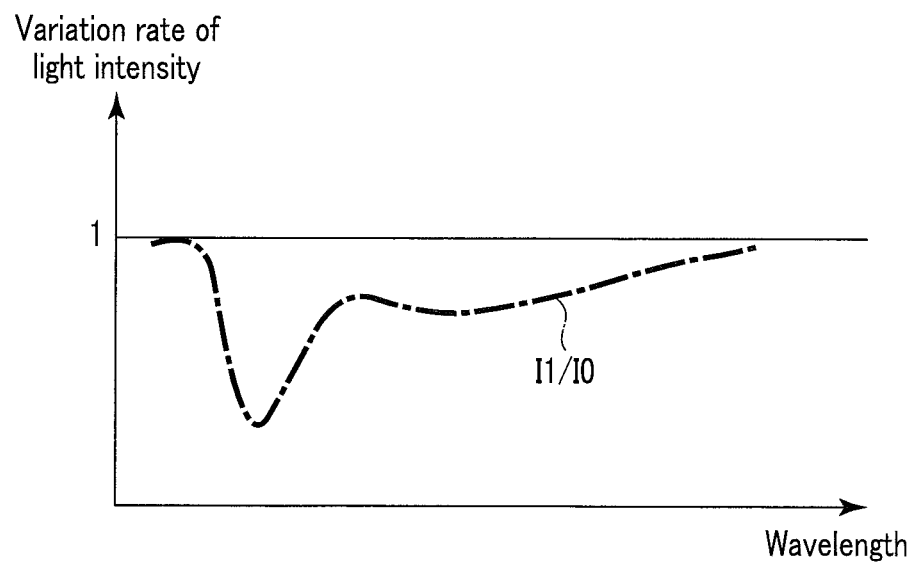
FIG. 6 is a diagram showing a variation ratio in light intensity at each wavelength, specifically showing a bend variation ratio of the first spectrum I1 in the bend state with respect to the first spectrum I0 in the reference state.

FIG. 6 shows a variation ratio of light intensity at each wavelength, specifically, a variation ratio (I1/I0) of the first spectrum I1 in the bend state with respect to the first spectrum I0 in the reference state. This variation ratio is hereinafter referred to as a bend variation ratio. The bend variation ratio is a variation ratio of a spectrum derived only from the bends of the detection targets 411, and is the third variation information.

Next, the second spectra Q0 and Q2 at times T0 and T2 will be described.

At the time T2, the detection targets 411 remain in the reference state, in which the spectrum of the light source 310 is varied. Thus, the second spectra Q0 and Q2 are not influenced by the bends of the detection targets 411.

Figure 7:
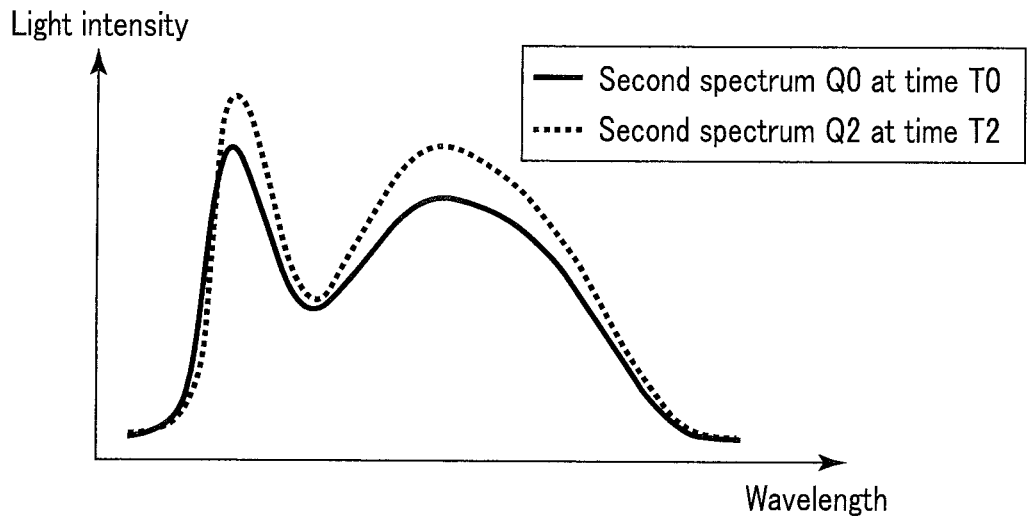
FIG. 7 is a diagram showing, in terms of a second spectrum representing a light intensity for each wavelength in a predetermined wavelength range, a relationship between a second spectrum Q0 at a time T0 and a second spectrum Q2 at a time T2.

FIG. 7 shows a relationship between the second spectra Q0 and Q2, which are light intensities for respective wavelengths in a predetermined wavelength range estimated by the spectrum estimation unit 623 at the time T0 and the time T2. The second spectrum Q0 indicates the second spectrum at the time T0. The second spectrum Q2 indicates the second spectrum at the time T2 when a predetermined time has elapsed from the time T0. For example, as a lapse of a predetermined time, the second spectrum Q2 varies with respect to the second spectrum Q0 by at least one of an ambient temperature around the light source 310, a drive current of the light source 310, heat generation of the light emitting element provided in the light source 310, and a temporal variation of the light source 310. The second spectra Q0 and Q2 become known by being estimated by the spectrum estimation unit 623.

Next, variation ratios of the second spectra Q0 and Q2 will be described.

Figure 8:
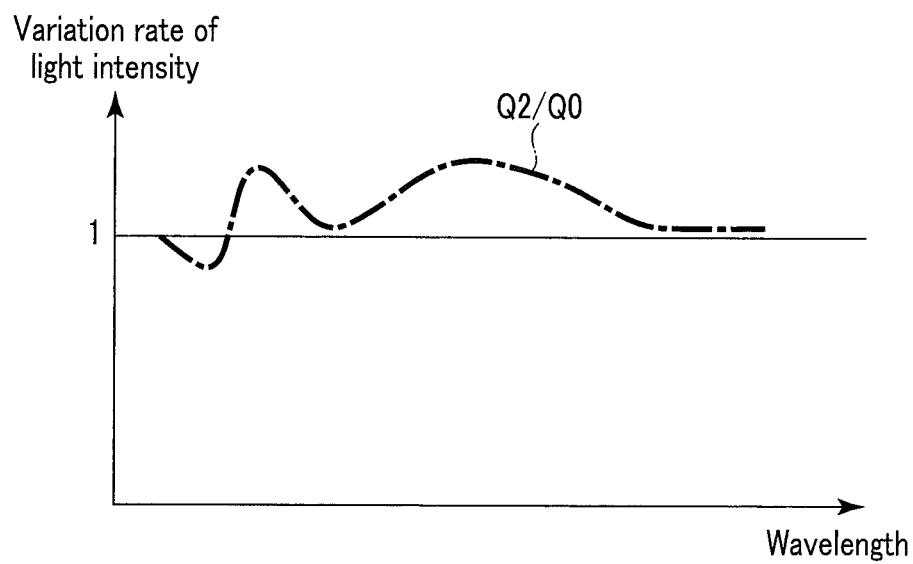
FIG. 8 is a diagram showing a variation ratio of light intensity at each wavelength, specifically showing a light source variation ratio of the second spectrum Q2 at the time T2 with respect to the second spectrum Q0 at the time T0.

FIG. 8 shows a variation ratio of light intensity at each wavelength, specifically, a variation ratio (Q2/Q0) of the second spectrum Q2 at the time T2 with respect to the second spectrum Q0 at the time T0. This variation ratio is hereinafter referred to as a light source variation ratio. The light source variation ratio is a variation ratio of the spectrum of the light source 310, and represents the first variation information. This light source variation ratio is, for example, arithmetically operated by the main body 605 of the generation unit 600, and is output to the bend information arithmetic operator 110 through the input unit 130. The light source variation ratio (Q2/Q0) becomes known because Q2 and Q0, which are known, are used.

Next, at a time T3 when a predetermined time has elapsed from the time T0, when the spectrum of the light source 310 varies from the second spectrum Q0 to the second spectrum Q2 similarly to the time T2, and the detection targets 411 remain in the reference state, a first spectrum I3 and a bend variation ratio (the third variation information) of light will be considered.

At the time T0, the detection targets 411 are in the reference state. At this time, it is defined that light of the first spectrum I0 is guided by the light guide 420, the light detection sensor 320 detects the first spectrum I0, and it is defined that the spectrum estimation unit 623 estimates the second spectrum Q0.

At the time T3 when a predetermined time has elapsed from the time T0, the detection targets 411 remain in the reference state, similarly to the time T0. In this case, it is defined that the spectrum estimation unit 623 estimates the spectrum Q2 at the time T3, similarly to the time T2. Since the detection targets 411 are in the reference state at the time T3, no variation in spectrum (the third variation information) derived only from the bend occurs. Thus, at the time T3, only a variation (the first variation information) in spectrum not derived from the bend occurs. In other words, since the detection targets 411 are in the reference state, the light detection sensor 320 should intrinsically detect the first spectrum I3 that is equal to the first spectrum I0, similarly to the time T0 shown in FIG. 5. However, since the first spectrum I3 at the time T3 detected by the light detection sensor 320 does not become equal to the first spectrum I0 due to the influence of the spectral variation of the light source 310, the second spectra Q0 and Q2 at the times T0 and T3 need to be considered. In this case, the first spectrum I3 is expressed by I0 ×Q2/Q0. As described above, even if the shape of the detection targets 411 does not change, the first variation information (light source variation ratio) not derived from the bend is overlapped on the first spectrum due to the variation in the spectrum of the light source 310.

A bend variation ratio of the first spectrum I3 at the time T3 (reference state) with respect to the first spectrum I0 at the time T0 (reference state) is I3/I0=Q2/Q0, and is arithmetically operated by the bend information arithmetic operator 110.

Next, a first spectrum I4 and the bend variation ratio (the third variation information) when at a time T4 when a predetermined time has elapsed from the time T0, the spectrum of the light source 310 varies from the second spectrum Q0 to the second spectrum Q2 similarly to the time T2, and the detection target 411 varies from the reference state to the bend state similarly to the time T1 will be considered.

At the time T0, the detection targets 411 are in the reference state. It is defined that, at this time, the light of the first spectrum I0 is guided by the light guide 420, and the light detection sensor 320 detects the first spectrum I0. In addition, it is defined that the spectrum estimation unit 623 estimates the second spectrum Q0.

Figure 9:
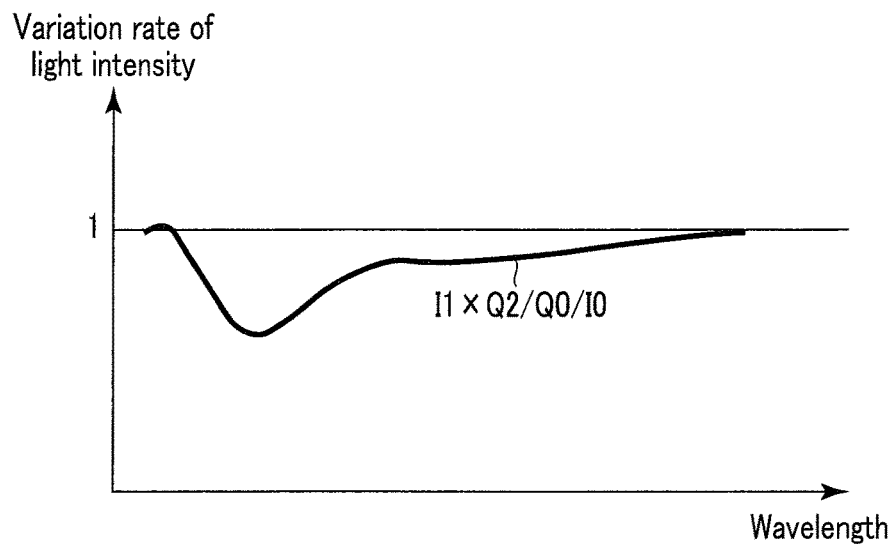
FIG. 9 is a diagram showing a variation ratio in light intensity at each wavelength, specifically showing a variation ratio of a first spectrum I4 in a bend state and at the time T4 with respect to the first spectrum I0 in the reference state and at the time T0.

At the time T4 when a predetermined time has elapsed from the time T0, unlike the time T0, the detection targets 411 are in the bend state. In this case, it is defined that the spectrum estimation unit 623 estimates the second spectrum Q2. Since the detection targets 411 are in the bend state, the light detection sensor 320 should intrinsically detect the first spectrum I4 that is equal to the first spectrum I1, similarly to the time T1 shown in FIG. 5. However, since the first spectrum I4 at the time T4 detected by the light detection sensor 320 does not become equal to the first spectrum I1 due to the influence of the spectral variation of the light source 310, the second spectra Q0 and Q2 at the times T0 and T4 need to be considered. In this case, the first spectrum I4 is expressed by I1×Q2/Q0. As shown in FIG. 9, a bend variation ratio of the first spectrum I4 at the time T4 (bend state) with respect to the first spectrum I0 at the time T0 (reference state) is expressed by I4/I0=(I1×Q2/Q0)/I0. This variation ratio is the second variation information including the first variation information (Q2/Q0), and is arithmetically operated by the bend information arithmetic operator 110. Since the second variation information includes the first variation information, the bend information arithmetically operated on the basis of the second variation information is different from actual bend information. Namely, an error occurs between the bend information arithmetically operated on the basis of the second variation information and the actual bend information due to the first variation information, and accurate bend information is not computed. Accordingly, it is necessary to suppress the first variation information and arithmetically operate the bend information based only on the third information shown in FIG. 6.

Figure 10:
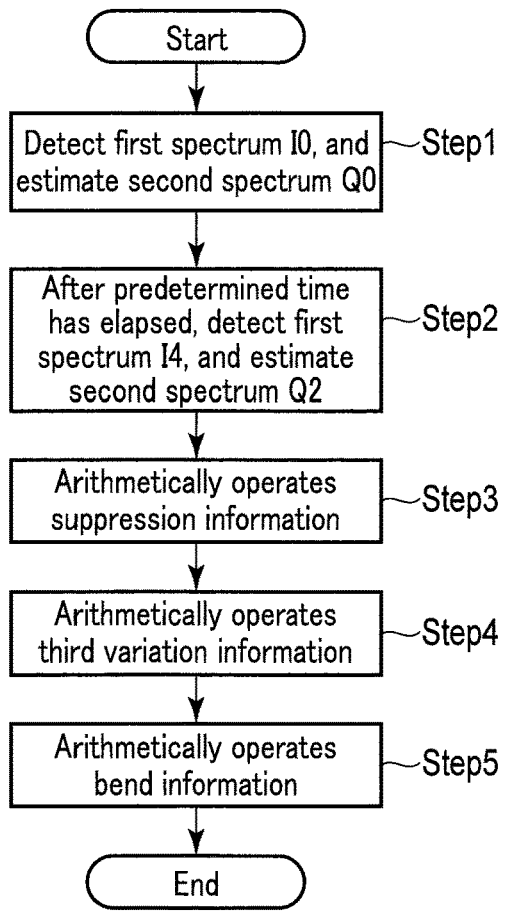
FIG. 10 is a flowchart showing a part of a flow of processing in a controller.

Therefore, referring to FIG. 10, a procedure that suppresses the first variation information and arithmetically operates the third variation information will be described. The detection targets 411 at the time T0 are in the reference state, the light detection sensor 320 detects the first spectrum I0, and the spectrum estimation unit 623 of the generation unit 600 estimates the second spectrum Q0 (Step 1).

The detection targets 411 at the time T4 when a predetermined time has elapsed from the time T0 are in the bend state, the light detection sensor 320 detects the first spectrum I4, and the spectrum estimation unit 623 of the generation unit 600 estimates the second spectrum Q2 (Step 2).

When considering the second spectra Q0 and Q2 at the times T0 and T4, the first spectrum I4 is expressed by I1×Q2/Q0. The bend variation ratio of the first spectrum I4 at the time T4 (bend state) with respect to the first spectrum I0 at the time T0 (reference state) is expressed by I4/I0=(I1×Q2/Q0)/I0.

In order to suppress the first variation information, the main body 605 of the generation unit 600 arithmetically operates the reciprocal of the light source variation ratio (Q2/Q0), which is the first variation information, as the suppression information that suppresses the first variation information in the second variation information (Step 3). That is, the main body 605 arithmetically operates Q0/Q2, which is the reciprocal, as the suppression information. Q0/Q2 is arithmetically operated on the basis of an estimation result of the spectrum estimation unit 623. Q0/Q2 becomes already known because Q2 and Q0, which are known, are used. The main body 605 outputs the suppression information to the bend information arithmetic operator 110 through the input unit 130.

The bend information arithmetic operator 110 arithmetically operates the second variation information (I4/I0) from the first spectra I0 and I4 stored in the storage 120, and arithmetically operates the third variation information on the basis of the second variation information (I4/I0) and the suppression information (Q0/Q2) (Step 4). Namely, the bend information arithmetic operator 110 extracts the third variation information from the second variation information. Therefore, the bend information arithmetic operator 110 performs arithmetic operation of the following equation (1).

$$(I4/I0) \times (Q0/Q2) = ((I1 \times Q2/Q0)/I0) \times (Q0/Q2) = I1/I0 = \ldots \quad (1)$$

In this manner, the bend information arithmetic operator 110 cancels the first variation information (Q2/Q0) from the second variation information (I4/I0) using the suppression information (Q0/Q2) to arithmetically operate the third variation information (I1/I0).

The bend information arithmetic operator 110 arithmetically operates the bend information (the direction of bend and the magnitude of bend) of each detection target 411 on the basis of the third variation information (Step 5).

The arithmetically operated bend information of each detection target 411 is acquired by the endoscope bend information calculator 140. The endoscope bend information calculator 140 calculates the bend information of the insertion section 812 based on the acquired bend information.

The bend information of each detection target 411 arithmetically operated by the bend information arithmetic operator 110 and the bend information of the insertion section 812 calculated by the endoscope bend information calculator 140 are acquired by the endoscope controller 820 through the output unit 160. The bend information is displayed on the display 180 through the output unit 160.

Furthermore, the information input into the input unit 130 and the bend information of each detection target 411 arithmetically operated by the bend information arithmetic operator 110 are acquired by the light detection sensor driver 150. The light detection sensor driver 150 transmits the driving signals to the light detection sensor 320 through the output unit 160 based on the acquired information, and controls the operation of the light detection sensor 320.

As described above, in the present embodiment, even if the second variation information includes the first variation information, it is possible to arithmetically operate the third variation information representing the variation in the spectrum derived only from the bends of the detection targets 411 by the suppression information. Therefore, even if an error occurs between the arithmetically operated bend information and the actual bend information, the error can be eliminated by the third variation information and accurate bend information can be computed. The error is an error derived from a variation in spectrum not derived from the bends of the detection targets 411. Furthermore, based on the acquired bend information, the endoscope bend information calculator 140 calculates the bend information of the insertion section 812, and the display 180 displays the bend information of the insertion section 812. Thereby, the user can ascertain the bend information of the insertion section 812 during operation of the endoscope 810.

In the present embodiment, the light source spectrum information storage 622 is provided, and suppression information is generated on the basis of the light source spectrum information stored in the light source spectrum information storage 622. In this embodiment, therefore, the generation of suppression information can eliminate a configuration of directly detecting the spectrum (second spectrum) of the light source 310.

It is assumed that this configuration for direct detection includes, for example, a light detection sensor (not shown) that detects light for detection emitted from the light source 310, i.e., light not modulated by the detection targets 411, without going through the detection targets 411, etc., and a branching unit (not shown) that branches the light emitted from the light source 310 into the light detection sensor. The light detection sensor is a detection sensor different from the light detection sensor 320. The branching unit includes, for example, a light guide different from the light guide 420. The light guide is optically connected to the light source 310 at one end, and is optically connected to the light detection sensor at the other end. The light guide guides light for detection emitted from the light source 310 to the light detection sensor without going through a detection targets, etc. As the branching section, a beam splitter, etc. that splits light into the light detection sensor can be used.

Therefore, in the present embodiment, only one light detection sensor 320 needs to be provided, branching into the light detection sensor can also be eliminated, and the cost of the computation apparatus 10 would not increase.

In addition, the configuration for direct detection may include the light detection sensor 320 and a switching device. The switching device shields, in the light detected by the light detection sensor 320, at least one of light not modulated by the detection targets 411 and light modulated by the detection targets 411.

In this embodiment, therefore, it is possible to reduce the trouble of switching, and to lower the cost of the computation apparatus 10 because a switching device is unnecessary.

The second spectrum is estimated by the spectrum estimation unit 623. Therefore, it is possible to eliminate a configuration for direct detection and eliminate branching and switching, and the cost of the computation apparatus 10 would not increase.

When the light source drive information is input from the light source drive information acquisition unit 621, the spectrum estimation unit 623 accesses the light source spectrum information storage 622. Then, the spectrum estimation unit 623 estimates the second spectrum by reading the second spectrum (the spectrum of the light source 310) corresponding to the light source drive information from the light source spectrum information storage 622. Therefore, even if the configuration for direct detection is not provided, the second spectrum can be detectable.

The light source drive information includes at least one of the drive current information of the light source 310, the temperature information of the light source 310, and the integrated drive time information of the light source 310. Thus, the spectrum estimation unit 623 can surely estimate the second spectrum.

The light source drive information acquisition unit 621 stores the light source spectrum information in advance, and the light source spectrum information has a relationship between the light source drive information and the spectrum of the light source 310. When the spectrum estimation unit 623 estimates the second spectrum, the spectrum estimation unit 623 only has to access the light source drive information acquisition unit 621, and thus can quickly estimate the second spectrum.

The drive measurement unit 627 measures at least one of the integrated drive time and the number of times of integrated drive of at least one of the light source 310 and the light detection sensor 320. Thus, in the present embodiment, the operation of the spectrum estimation unit 623 can be controlled in the following manner.

The spectrum estimation unit 623 estimates the second spectrum Q0, for example, at the time of calibration. This calibration is performed, for example, when the detection targets 411 are in a predetermined state such as a linear state and a predetermined number of times of operation of the detection targets 411 is finished by a measurement result of the drive measurement unit 627. The predetermined state indicates, for example, a known state, such as a reference state. The calibration may be necessarily performed when the endoscope 810 is connected to the computation apparatus 10, or may be performed at a desired timing.

That is, the spectrum estimation unit 623 estimates the second spectrum Q2 at one of the following timings 1 to 5, for example.

As a timing 1, for example, every time the light detection sensor 320 detects the first spectrum I1, the spectrum estimation unit 623 estimates the second spectrum Q2. That is, the estimation timing of the spectrum estimation unit 623 coincides with the timing of the light detection sensor 320.

As a timing 2, for example, when the light detection sensor 320 detects the first spectrum I1 a predetermined number of times, the spectrum estimation unit 623 estimates the second spectrum Q2. That is, the detection timing of the spectrum estimation unit 623 is fewer than the timing of the light detection sensor 320. For example, when the light detection sensor 320 detects ten times, the spectrum estimation unit 623 estimates one time.

With the use of the drive measurement unit 627, the following timing can also be included.

As a timing 3, the spectrum estimation unit 623 estimates the second spectrum Q2 at predetermined time intervals. That is, the spectrum estimation unit 623 independently estimates without being influenced by the light detection sensor 320. The spectrum estimation unit 623 detects once a second, for example.

As a timing 4, when the temperature of the light source 310 varies over a predetermined range, the spectrum estimation unit 623 detects the second spectrum Q2. For example, if the temperature of the light source 310 changes to ±0.2° or more from a desired value, the spectrum estimation unit 623 estimates the second spectrum Q2.

As a timing 5, on the basis of the drive current flowing through the light source 310, the spectrum estimation unit 623 estimates the second spectrum Q2 when brightness of the light source 310 changes.

In this way, the spectrum estimation unit 623 estimates the second spectrum Q2 when the detection targets 411 are in a predetermined state and a predetermined number of times of operation of the detection target 411 is finished, when a predetermined time has elapsed, when a predetermined temperature change occurs in the light source 310, or when an operating state of the light source 310 is changed.

When a difference between the second spectrum Q0 and the second spectrum Q2 is small and the light source variation ratio (Q2/Q0) is approximately close to 1, in order to reduce a load of the bend information arithmetic operator 110, the main body 605 may set suppression information to 1.

In the case where a wavelength band in which the first variation information appears conspicuously is known in advance, in order to reduce the load of the bend information arithmetic operator 110, the main body 605 may generate suppression information only in that wavelength band.

In the bend information arithmetic operator 110, the bend of the insertion section 812 is raised as an example of computation, but it does not need to be limited to this, and may be detection of distortion for health monitoring of a structure.

The light detection sensor 320 may be composed of an element that transmits only light with a predetermined wavelength range such as a color filter, and a light receiving element such as a photodiode.

The present invention is not limited to the above embodiment as it is, and structural elements can be modified and embodied without departing from the gist thereof in the implementation stage. Furthermore, various inventions can be formed by appropriately combining a plurality of structural elements disclosed in the above embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A controller comprising:
a processor comprising hardware, the processor being configured to:
acquire a first spectrum representing an intensity of first light guided by a fiber from a light source that emits light to the fiber;
acquire a second spectrum representing an intensity of second light emitted from the light source to the fiber; and
calculate bend information of the fiber based on the first spectrum and the second spectrum;
wherein the processor is configured to:
generate, from the second spectrum, suppression information to correct a variation in intensity of light included in the first spectrum and derived from the light source; and
calculate the bend information of the fiber based on the first spectrum and the suppression information; and
the processor is configured to:
acquire light source drive information of the light source;
estimate the second spectrum from the light source drive information; and
generate the suppression information from the second spectrum.

2. The controller according to claim 1, wherein the processor is configured to:
calculate, based on the second spectrum, first variation information representing a variation in intensity of light derived from the light source; and
generate the suppression information based on the first variation information.

3. The controller according to claim 2, wherein the processor is configured to:
calculate, based on the first spectrum, second variation information including the first variation information and representing a variation in spectrum derived from a bend of the fiber;
calculate, based on the second variation information and the suppression information, third variation information not including the first variation information and representing a variation in spectrum derived only from the bend; and
calculate the bend information of the fiber based on the third variation information.

4. The controller according to claim 1, wherein the light source drive information includes at least one of drive current information of the light source, temperature information of the light source, and integrated drive time information of the light source.

5. The controller according to claim 1, wherein the first spectrum is a spectrum of light reflected from a distal end of the fiber.

6. A bend information computation apparatus comprising:
a fiber that guides light;
a light source that emits the light to the fiber;
a light detection sensor that detects a first spectrum representing an intensity of first light guided by the fiber;
a detection target provided in the fiber; and
a controller comprising a processor, the processor being configured to:
acquire the first spectrum representing the intensity of the first light guided by the fiber;
acquire a second spectrum representing an intensity of second light emitted from the light source to the fiber; and
calculate bend information of the fiber based on the first spectrum and the second spectrum;
wherein the processor is configured to:
generate, from the second spectrum, suppression information to correct a variation in intensity of light included in the first spectrum and derived from the light source; and
calculate the bend information of the fiber based on the first spectrum and the suppression information; and
the processor is configured to:
acquire light source drive information of the light source;
estimate the second spectrum from the light source drive information; and
generate the suppression information from the second spectrum.

7. The bend information computation apparatus according to claim 6, wherein the first spectrum is a spectrum of light reflected from a distal end of the fiber.

8. A bend information computation method comprising:
acquiring a first spectrum representing an intensity of first light guided by a fiber from a light source that emits light to the fiber;
acquiring a second spectrum representing an intensity of second light emitted from the light source to the fiber; and calculating bend information of the fiber based on the first spectrum and the second spectrum;

further comprising:

generating, from the second spectrum, suppression information to correct a variation in intensity of light included in the first spectrum and derived from the light source; and calculating the bend information of the fiber based on the first spectrum and the suppression information;

further comprising:

acquiring light source drive information of the light source;

estimating the second spectrum from the light source drive information; and generating the suppression information from the second spectrum.

9. The bend information computation method according to claim 8, wherein the first spectrum is a spectrum of light reflected from a distal end of the fiber.

* * * * *